United States Patent
Laborde et al.

(10) Patent No.: US 7,872,134 B2
(45) Date of Patent: *Jan. 18, 2011

(54) 2-{[2-(SUBSTITUTED AMINO)ETHYL]SULFONYL}ETHYL N,N-BIS(2-CHLOROETHYL) PHOSPHORODIAMIDATES

(75) Inventors: Edgardo Laborde, Foster City, CA (US); Andrew B. Kelson, San Carlos, CA (US); Wenli Ma, Union City, CA (US); Kevin T. Weber, Carmel, IN (US)

(73) Assignee: Telik, Inc., Palo Alto, CA (US)

( * ) Notice: Subject to any disclaimer, the term of this patent is extended or adjusted under 35 U.S.C. 154(b) by 569 days.

This patent is subject to a terminal disclaimer.

(21) Appl. No.: 11/955,177

(22) Filed: Dec. 12, 2007

(65) Prior Publication Data
US 2009/0156559 A1 Jun. 18, 2009

(51) Int. Cl.
*C07F 9/572* (2006.01)
*C07F 9/576* (2006.01)
*C07F 9/24* (2006.01)
*A61K 31/664* (2006.01)
*A61K 31/675* (2006.01)

(52) U.S. Cl. .................. 546/22; 548/413; 558/169; 514/89; 514/91; 514/118

(58) Field of Classification Search .................. 546/22; 558/169; 514/89, 91, 118; 548/413
See application file for complete search history.

(56) References Cited

U.S. PATENT DOCUMENTS

| 5,556,942 A | 9/1996 | Kauvar et al. |
| 6,506,739 B1 | 1/2003 | Herr et al. |
| 7,655,799 B2 * | 2/2010 | Ma et al. ............ 546/22 |
| 2005/0267075 A1 | 12/2005 | Robinson et al. |

FOREIGN PATENT DOCUMENTS

| WO | WO 95/09866 A1 | 4/1995 |
| WO | WO 01/83496 A1 | 11/2001 |
| WO | WO 2005/118601 A2 | 12/2005 |

OTHER PUBLICATIONS

Jain M et al., "Sulfonyl-containing aldophosphamide analogues as novel anticancer prodrugs targeted against cyclophosphamide-resistant tumor cell lines", *J. Med. Chem.*, v.47, pp. 3843-3852, Jul. 15, 2004 (published on Web Jun. 17, 2004).
Tew, K.D. "TLK-286: A novel glutathione S-transferase-activated prodrug." *Expert Opinion on Investigational Drugs*, Ashley Publications Ltd., Londn, GB, vol. 14, No. 8, 2005, pp. 1047-1054.
U.S. Appl. No. 11/564,744, Ma et al.

* cited by examiner

*Primary Examiner*—Janet L Andres
*Assistant Examiner*—Timothy R Rozof
(74) *Attorney, Agent, or Firm*—Foley & Lardner LLP

(57) ABSTRACT

2-{[2-(Substituted amino)ethyl]sulfonyl}ethyl N,N-bis(2-chloroethyl)phosphorodiamidates and their salts, their preparation and intermediates in their preparation, pharmaceutical compositions containing them, and methods of treatment using them. The compounds are useful for treating cancer and autoimmune diseases, alone and in combination with other therapies.

13 Claims, No Drawings

2-{[2-(SUBSTITUTED AMINO)ETHYL]SULFONYL}ETHYL N,N-BIS(2-CHLOROETHYL) PHOSPHORODIAMIDATES

BACKGROUND OF THE INVENTION

1. Field of the Invention

This invention relates to 2-{[2-(substituted amino)ethyl]sulfonyl}ethyl N,N-bis(2-chloroethyl)-phosphorodiamidates and their salts, pharmaceutical compositions containing them, their pharmaceutical use, and their preparation and intermediates in their preparation.

2. Description of the Related Art

U.S. Pat. No. 5,556,942 [and PCT Publication No. WO 95/09865] discloses compounds of the formula

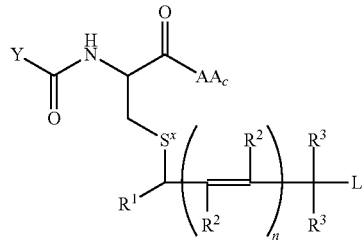

and their amides, esters, and salts, where:

L is an electron withdrawing leaving group;

$S^x$ is —S(=O)—, —S(=O)$_2$—, —S(=NH)—, —S(=O)(=NH)—, —S$^+$(C$_1$-C$_6$ alkyl)-, —Se(=O)—, —Se(=O)$_2$—, —Se(=NH)—, or —Se(=O)(=NH)—, or is —O—C(=O)—, or —HN—C(=O)—;

each $R^1$, $R^2$ and $R^3$ is independently H or a non-interfering substituent;

n is 0, 1 or 2;

Y is selected from the group consisting of

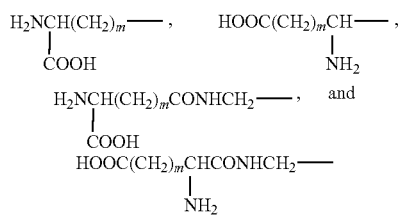

where m is 1 or 2; and $AA_c$ is an amino acid linked through a peptide bond to the remainder of the compound.

The compounds are stated to be useful drugs for the selective treatment of target tissues which contain compatible glutathione S-transferase (GST) isoenzymes, and simultaneously elevate the levels of granulocyte macrophage progenitor cells in bone marrow. Disclosed embodiments for L include those that generate a drug that is cytotoxic to unwanted cells, including the phosphoramidate and phosphorodiamidate mustards.

PCT Publication No. WO 95/09865 also discloses intermediates that are compounds of the formula

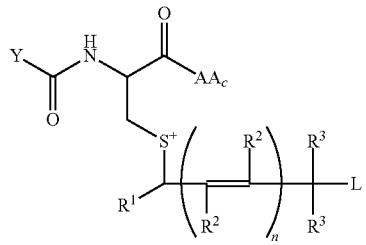

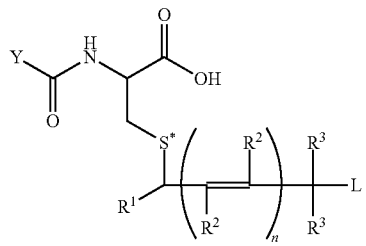

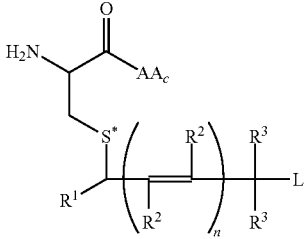

and their amides, esters, and salts, where:

L is an electron withdrawing leaving group;

$S^+$ is S or Se;

$S^*$ is —S(=O)—, —S(=O)$_2$—, —S(=NH)—, —S(=O)(=NH)—, —S$^+$(C$_1$-C$_6$ alkyl)-, —Se(=O)—, —Se(=O)$_2$—, —Se(=NH)—, or —Se(=O)(=NH)—, or is —O—C(=O)—, or —HN—C(=O)—;

each $R^1$, $R^2$ and $R^3$ is independently H or a non-interfering substituent;

n is 0, 1 or 2;

Y is selected from the group consisting of

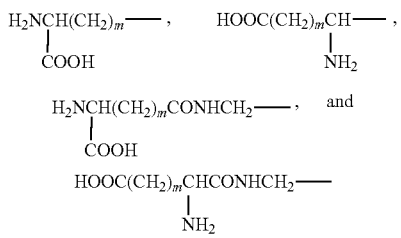

where m is 1 or 2; and $AA_c$ is an amino acid linked through a peptide bond to the remainder of the compound.

U.S. Pat. No. 6,506,739 [and PCT Publication No. WO 01/83496] discloses compounds of the formula

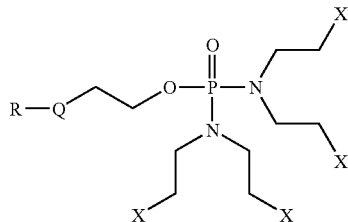

where:

X is a halogen atom;

Q is O, S, or NH; and

R is hydrogen, optionally substituted lower alkyl, optionally substituted aryl, or optionally substituted heteroaryl, or is R'CO—, R'NHCO—, R'SO$_2$—, or R'NHSO$_2$— where R' is hydrogen, optionally substituted lower alkyl, optionally substituted aryl, or optionally substituted heteroaryl; or R-Q together is chlorine; and their salts, as antitumor agents.

US Patent Application Publication No. 2005/0267075 [and PCT Publication No. WO 2005/118601] discloses compounds of the formulae

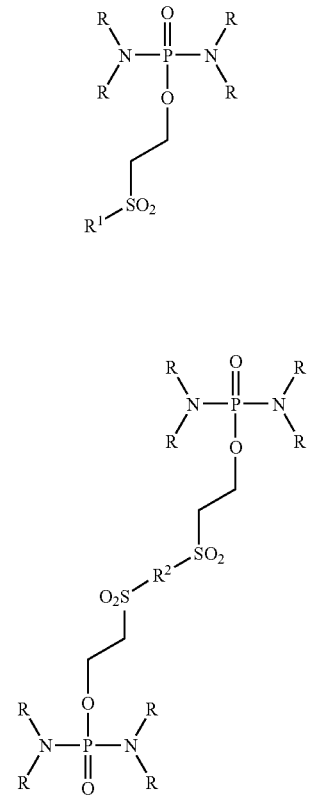

where:

each R is independently hydrogen, $C_{1-6}$ alkyl, or —CH$_2$CH$_2$X, where each X is independently Cl, Br, $C_{1-6}$ alkanesulfonyloxy, halo-$C_{1-6}$ alkanesulfonyloxy, or benzenesulfonyloxy optionally substituted with up to three substituents selected from halo, $C_{1-3}$ alkyl, halo-$C_{1-3}$ alkyl, $C_{1-3}$ alkyloxy, or halo-$C_{1-3}$ alkyloxy, provided that at least two R's in each phosphorodiamidate group are —CH$_2$CH$_2$X;

$R^1$ is optionally substituted alkyl, optionally substituted heteroalkyl, optionally substituted aryl, optionally substituted aralkyl, optionally substituted heteroaryl, or optionally substituted heteroaralkyl; and $R^2$ is optionally substituted alkanediyl, optionally substituted heteroalkanediyl, optionally substituted arenediyl, optionally substituted arenedialkyl, optionally substituted heteroarenediyl, or optionally substituted heteroarenedialkyl, and their salts, as antitumor agents.

Jain et al., "Sulfonyl-containing aldophosphamide analogues as novel anticancer prodrugs targeted against cyclophosphamide-resistant tumor cell lines", *J. Med. Chem.*, 47(15), 3843-3852 (2004), discloses a series of sulfonylethyl phosphorodiamidates of the formula

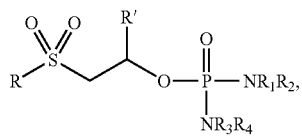

including compounds where $R_1$=$R_2$=CH$_2$CH$_2$Cl, $R_3$=$R_4$=H; $R_1$=$R_3$=CH$_2$CH$_2$Cl, $R_2$=$R_4$=H; and $R_1$=$R_2$=$R_3$=$R_4$=CH$_2$CH$_2$Cl. The compounds are said to spontaneously liberate phosphoramide mustards via beta-elimination, and to be more potent than the corresponding phosphoramide mustards against V-79 Chinese hamster lung fibroblasts in vitro. Some of the compounds were said to show excellent in vivo antitumor activity in CD2F1 mice against the P388/0 (wild) and P388/CPA (cyclophosphamide-resistant) leukemia cell lines.

U.S. patent application Ser. No. 11/564,744 discloses compounds of the formula

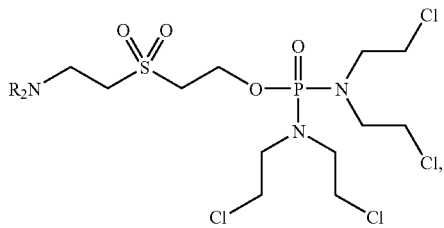

and their salts, where each R is independently methyl, ethyl, propyl, or isopropyl, or —NR$_2$ together is 1-pyrrolidinyl or 1-piperidinyl, as antitumor agents.

Cyclophosphamide is used for the treatment of a number of cancers (including lymphomas, multiple myeloma, leukemias, mycosis fungoides, neuroblastoma, ovarian adenocarcinoma, retinoblastoma, and breast carcinoma) and, at lower doses, for the treatment of autoimmune diseases (including lupus, scleroderma, vasculitis, myopathies, and complications of rheumatoid arthritis). It is metabolically activated by enzymes in the liver to release acrolein and "cyclophosphamide mustard", as follows:

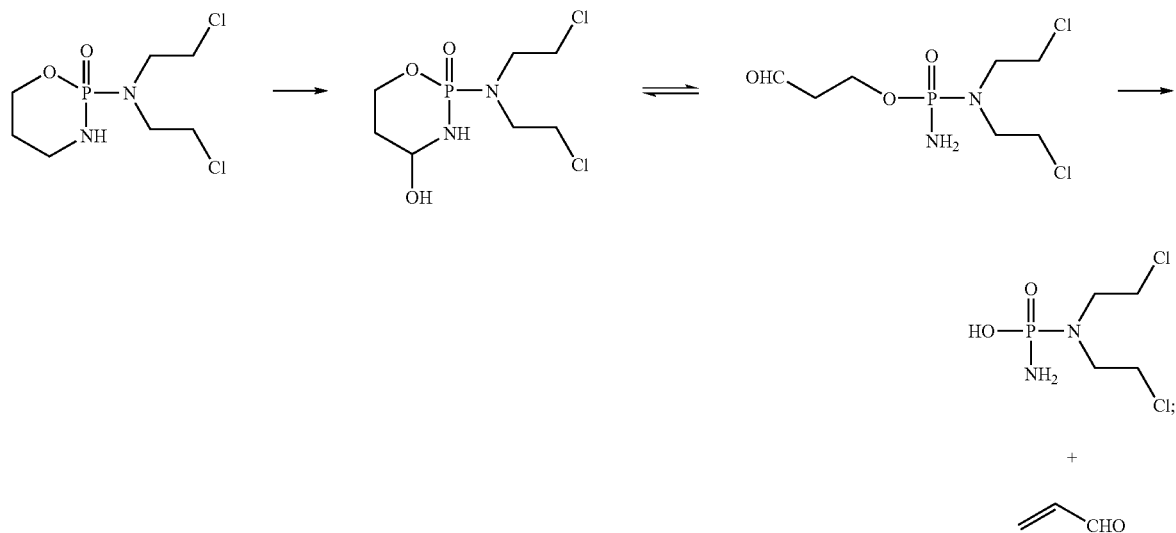

and some of the toxicities of cyclophosphamide (in particular, cystitis) are attributed to the acrolein.

It would be desirable to develop chemically and pharmaceutically simple (easy to synthesize and formulate) compounds having an efficacy and safety as good as or better than cyclophosphamide.

The complete disclosures of the documents referred to in this application are incorporated into this application by reference.

SUMMARY OF THE INVENTION

In a first aspect, this invention is 2-{[2-(substituted amino)ethyl]sulfonyl}ethyl N,N-bis(2-chloroethyl)phosphorodiamidates, compounds of formula A:

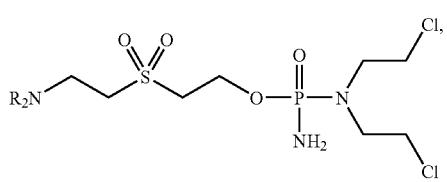

and their salts, where each R is independently methyl, ethyl, propyl, or isopropyl, or —NR$_2$ together is 1-pyrrolidinyl or 1-piperidinyl.

These compounds release "cyclophosphamide mustard", but do not require metabolic activation and do not produce acrolein when the "cyclophosphamide mustard" is released.

In a second aspect, this invention is pharmaceutical compositions comprising a compound of the first aspect of this invention.

In a third aspect, this invention is methods of treating cancers and autoimmune diseases by the administration of a compound of the first aspect of this invention or a pharmaceutical composition of the second aspect of this invention; alone or in combination with other therapies for the condition being treated.

In a fourth aspect, this invention is methods of preparing compounds of the first aspect of this invention, and intermediates in the methods.

DETAILED DESCRIPTION OF THE INVENTION

Definitions

"Salts" are described in the section entitled "Compounds of this invention".

A "therapeutically effective amount" means that amount which, when administered to a human for treating a disease, is sufficient to effect treatment for that disease. "Treating" or "treatment" of a cancer in a human includes one or more of:

(1) limiting/inhibiting growth of the cancer, i.e., limiting/arresting its development, (2) reducing/preventing spread of the cancer, i.e. reducing/preventing metastases, (3) relieving the cancer, i.e., causing regression of the cancer, (4) reducing/preventing recurrence of the cancer, and (5) palliating symptoms of the cancer;

while "treating" or "treatment" of an autoimmune disease in a human includes one or more of:

(1) relieving the autoimmune disease, i.e., causing regression of the autoimmune disease, (2) reducing/preventing recurrence of the autoimmune disease, and (3) palliating symptoms of the autoimmune disease.

"Combination therapy" means the administration of a compound of the first aspect of this invention and another therapy for the disease being treated. Such combination therapy may involve the administration of the compound of the first aspect of this invention before, during, and/or after the administration of the another therapy. The administration of the compound of the first aspect of this invention may be separated in time from the administration of the another therapy by up to several weeks, and may precede it or follow it, but more commonly the administration of the compound of the first aspect of this invention will accompany at least one aspect of the another therapy within up to 48 hours, and most commonly within less than 24 hours.

"Another therapy" is a therapy for the disease (cancer or an autoimmune disease) that is not a treatment with a compound of the first aspect of this invention. Such "another therapies" for cancer include chemotherapy; molecular targeted therapy; biologic therapy; and radiotherapy; and such "another therapies" for autoimmune diseases include steroids, non-steroidal anti-inflammatory drugs, immunosuppressants, and a wide variety of other therapies. These therapies are those used as monotherapy or in combination therapy.

Chemotherapeutic agents for cancer include:

alkylating agents, antimetabolites, natural products including antitumor antibiotics, anthracyclines, enzymes, taxanes, vinca alkaloids, camptothecins, and etoposide, hormones and hormone antagonists, and miscellaneous agents, including altretamine, arsenic trioxide, gallium nitrate, hydroxyurea, levamisole, mitotane, octreotide, procarbazine, suramin, thalidomide, lenalidomide, photodynamic compounds such as methoxsalen and sodium porfimer, and proteasome inhibitors such as bortezomib.

Molecular targeted therapy agents for cancer include:

functional therapeutic agents, phenotype-directed therapy agents including monoclonal antibodies, and cancer vaccines.

Biologic therapy agents for cancer include interferons and interleukins.

In addition to these agents intended to act against cancer cells, anticancer therapies include the use of protective or adjunctive agents, including:

cytoprotective agents such as amifostine, dexrazoxane, and mesna, phosphonates such as pamidronate and zoledronic acid, and stimulating factors such as epoetin, darbeopetin, filgrastim, PEG-filgrastim, and sargramostim.

Combination cancer therapy regimens with which the compounds of the first aspect of this invention may be combined include all regimens involving the use of two or more of the anticancer therapies (anticancer agents) such as those mentioned in paragraphs [0020] to [0022] above and/or radiotherapy, optionally including protective and adjunctive agents such as those mentioned in paragraph [0023] above; and the compound of the first aspect of this invention can be added to existing anticancer regimens known for the treatment of various cancers, such as the regimens mentioned in such books as Chabner and Longo, eds., "Cancer Chemotherapy and Biotherapy: Principles and Practice", 3rd ed. (2001), and Skeel, ed., "Handbook of Cancer Chemotherapy", $6^{th}$ ed. (2003), both from Lippincott Williams & Wilkins, Philadelphia, Pa., U.S.A.; and regimens for anticancer therapies, especially chemotherapies, may be found on Web sites such as those maintained by the National Cancer Institute (www.cancer.gov), the American Society for Clinical Oncology (www.asco.org), and the National Comprehensive Cancer Network (www.nccn.org).

"Comprising" or "containing" and their grammatical variants are words of inclusion and not of limitation and mean to specify the presence of stated components, groups, steps, and the like but not to exclude the presence or addition of other components, groups, steps, and the like. Thus "comprising" does not mean "consisting of", "consisting substantially of", or "consisting only of"; and, for example, a pharmaceutical composition "comprising" a compound must contain that compound but may also contain other active ingredients and/or excipients.

Compounds of this Invention

Representative compounds of the invention are those where each R is independently methyl, ethyl, or isopropyl; and where each R is the same; and where —$NR_2$ is dimethylamino, diethylamino (compound 1A), diisopropylamino, pyrrolidin-1-yl, or piperidin-1-yl, and their acid addition salts.

Salts (for example, pharmaceutically acceptable salts) of the compounds of formula A are included in the present invention and are useful in the compositions, methods, and uses described in this application. Suitable salts are acid addition salts formed when inorganic acids (e.g. hydrochloric, hydrobromic, sulfuric, nitric, phosphoric, and chlorosulfonic acids) or organic acids (e.g. acetic, propionic, oxalic, malic, maleic, malonic, fumaric, citric, tartaric, lactic, succinic, and aceturic acids, and alkane- or arenesulfonic acids such as methanesulfonic, ethanesulfonic, 2-hydroxyethanesulfonic, benzenesulfonic, substituted benzenesulfonic such as chlorobenzenesulfonic and toluenesulfonic, naphthalenesulfonic and substituted naphthalenesulfonic, naphthalenedisulfonic and substituted naphthalenedisulfonic, and camphorsulfonic acids) react to form acid addition salts of the amine groups of the compounds. Such salts are preferably formed with pharmaceutically acceptable acids. See, for example, Stahl and Wermuth, eds., "Handbook of Pharmaceutically Acceptable Salts", (2002), Verlag Helvetica Chimica Acta, Zürich, Switzerland, for an extensive discussion of pharmaceutical salts, their selection, preparation, and use.

Because the phosphorus atom of the compounds of the first aspect of invention has four different substituents, it is a chiral center; and the compounds of the first aspect of this invention are therefore capable of existing as two enantiomeric, optically active forms. The disclosure of a compound of the first aspect of this invention by name or formula is therefore intended to contemplate each of the two enantiomers and mixtures of the enantiomers in any proportions, such as racemic mixtures. Typically, the compounds will be prepared as racemic mixtures. However, it is possible to separate the enantiomers, if desired, by conventional means of resolution of basic compounds such as formation of diastereomeric acid addition salts with chiral acids such as D- or L-camphorsulfonic acid and the like, or by chiral chromatography. Although the compounds of the first aspect of this invention are chiral, the "cyclophosphamide mustard" produced by their decomposition is achiral because its two oxygen atoms are equivalent through proton exchange (in the acid form) and resonance (in the anion form).

Preparation of the Compounds

Compounds of formula A and their salts may conveniently be prepared by reacting N,N-bis(2-chloroethyl)phosphoramidic dichloride and a 2-[2-($NR_2$)-ethylthio]ethanol, followed by reaction with ammonia, to form a thioethyl phosphorodiamidate of formula B:

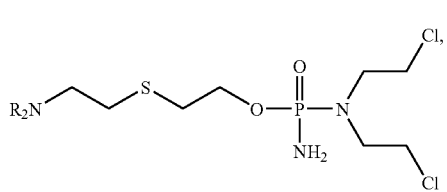

followed by oxidizing the sulfide to the corresponding sulfone of formula A, optionally followed by forming a salt of the compound of formula A.

The method is shown below:

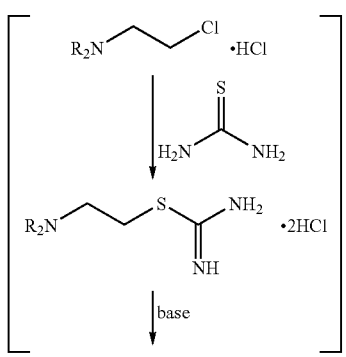

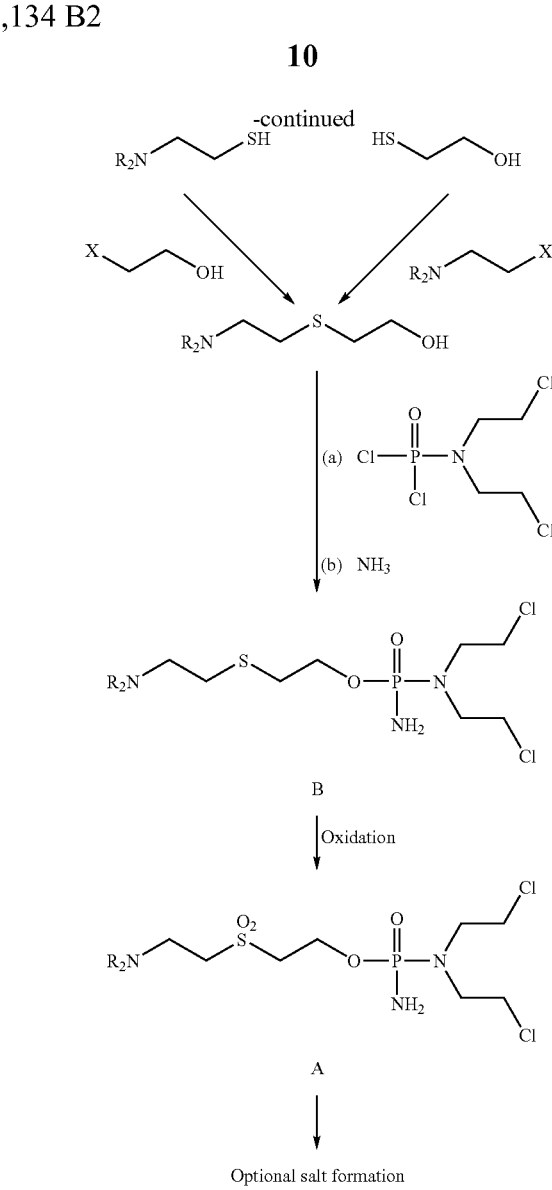

2-[2-($NR_2$)-Ethylthio]ethanols may conveniently be prepared by:

(1) the reaction of a 2-($NR_2$)-ethanethiol with a 2-X-ethanol (where X is a leaving group such as Br, Cl, $C_{1-6}$ alkanesulfonyloxy, halo-$C_{1-6}$ alkanesulfonyloxy, or benzenesulfonyloxy optionally substituted with up to three substituents selected from halo, $C_{1-3}$ alkyl, halo-$C_{1-3}$ alkyl, $C_{1-3}$ alkyloxy, or halo-$C_{1-3}$ alkyloxy, such as methanesulfonyloxy, benzenesulfonyloxy, 4-bromobenzenesulfoxy, or 4-toluenesulfonyloxy); or (2) the reaction of 2-mercaptoethanol with a 1-($NR_2$)-2-X-ethane.

A typical procedure for method (1) involves treating the 2-($NR_2$)-ethanethiol with a polar solvent such as water, an alkanol, dimethylformamide, or tetrahydrofuran, and a base such as a hydroxide, alkoxide, fluoride, or hydride, or a tertiary amine or amide base to form the thiolate anion, followed by adding the 2-X-ethanol (typically 2-bromoethanol or 2-chloroethanol). Thiolate displacement of the leaving group X of the 2-X-ethanol gives the 2-[2-($NR_2$)-ethylthio]ethanol.

2-(Dimethylamino)ethanethiol and 2-(diethylamino)ethanethiol are both readily commercially available as the hydrochloride salts. When the 2-($NR_2$)-ethanethiol is not available, it may be prepared by a method such as reacting a 2-($NR_2$)-ethyl halide [the chloride is shown in the reaction scheme above] with thiourea to prepare a 2-($NR_2$)-ethylisothiourea, which may be isolated as an acid addition salt if desired. When the 2-($NR_2$)-ethylisothiourea is treated with base, the corresponding 2-($NR_2$)-ethanethiolate is formed in solution, and the resulting solution may be used directly in the formation of the 2-[2-($NR_2$)-ethylthio]ethanol. A typical procedure involves treating a 2-($NR_2$)-ethyl chloride hydrochloride with thiourea in a lower alkanol, such as ethanol, at elevated temperature. On cooling, the isothiourea precipitates as a dihydrochloride salt, which may be isolated by filtration. The isothiourea is suspended in a lower alkanol and treated with base to form the thiolate anion, followed by adding the 2-X-ethanol. Thiolate displacement of the leaving group X of the 2-X-ethanol gives the 2-[2-($NR_2$)-ethylthio]ethanol. This method is illustrated in Preparative Example 1.

A typical procedure for method (2) involves treating the 2-mercaptoethanol with a polar solvent such as water, an alkanol, dimethylformamide, or tetrahydrofuran, and a base such as a hydroxide, alkoxide, fluoride, or hydride, or a tertiary amine or amide base to form the thiolate anion, followed by adding the 1-($NR_2$)-2-X-ethane (typically a 1-($NR_2$)-2-bromoethane or 1-($NR_2$)-2-chloroethane). Thiolate displacement of the leaving group X of the 1-($NR_2$)-2-X-ethane gives the 2-[2-($NR_2$)-ethylthio]ethanol. This method is illustrated in Preparative Example 2.

N,N-Bis(2-chloroethyl)phosphoramidic dichloride may conveniently be prepared by the reaction of bis(2-chloroethyl)amine hydrochloride with phosphoryl chloride. An efficient method is described in Friedman et al., "Preparation of N-Phosphorylated Derivatives of Bis-β-chloroethylamine", *J. Amer. Chem. Soc.*, 76, 655-658 (1954). There, a suspension of bis(2-chloroethyl)amine hydrochloride in about a 5-fold molar excess of phosphoryl chloride is refluxed until the reaction is complete, the excess phosphoryl chloride is removed by distillation, and the residue is distilled under reduced pressure to give N,N-bis(2-chloroethyl)phosphoramidic dichloride. Alternatively, as described in Preparative Example 3, the reaction may be conducted at reduced temperature in the presence of a solvent and a base, using equimolar amounts of bis(2-chloroethyl)amine hydrochloride and phosphoryl chloride.

In the first step of the synthesis of the compounds of formula A, the 2-[2-($NR_2$)-ethylthio]-ethanol is reacted first with N,N-bis(2-chloroethyl)phosphoramidic dichloride, and then with ammonia, to form a thioethyl phosphorodiamidate of formula B. A typical procedure involves treating the 2-[2-($NR_2$)-ethylthio]ethanol with a polar solvent such as tetrahydrofuran and a base such as an alkali metal hydride or amide, addition of the N,N-bis(2-chloroethyl)phosphoramidic dichloride, and then addition of ammonia to give the thioethyl phosphorodiamidate of formula B.

In the second step, the thioethyl phosphorodiamidate of formula B is oxidized to the corresponding sulfonylethyl phosphorodiamidate of formula A. This oxidation may be performed by any of the methods known in the art for the oxidation of sulfides to sulfones, such as the use of peracids (peroxycarboxylic acids), persulfates, perborates, peroxides, ozone, iodosyl reagents, halogens, and the like. Where a peracid is used, a typical procedure involves dissolving the thioethyl phosphorodiamidate in a solvent such as dichloromethane, acetic acid, or isopropyl acetate at reduced temperature, followed by the addition of the peracid (e.g. peracetic acid) in excess. The oxidation is performed under conditions that minimize oxidation of the amine nitrogen, such as by performing the oxidation at a sufficiently low pH to stabilize the amine as an ammonium cation.

Compounds of formula A may be converted to salts by reaction with the appropriate acids, using techniques well known to a person of ordinary skill in the art for the formation of acid addition salts. The acid used, and the reaction conditions, may be chosen to give salts that are pharmaceutically acceptable and that have a form convenient for isolation and formulation, such as a solid form (for example, amorphous or crystalline).

Pharmaceutical Compositions and Administration

The compounds of the first aspect of this invention may be administered by any route suitable to the subject being treated and the nature of the subject's condition. Routes of administration include administration by injection, including intravenous, intraperitoneal, intramuscular, and subcutaneous injection, by transmucosal or transdermal delivery, through topical applications, nasal spray, suppository and the like or may be administered orally. Pharmaceutical compositions may optionally be liposomal compositions, emulsions, compositions designed to administer the drug across mucosal membranes or transdermal compositions. Suitable compositions for each of these methods of administration may be found, for example, in Gennaro, ed., "Remington: The Science and Practice of Pharmacy", 20th ed. (2000), Lippincott Williams & Wilkins, Philadelphia, Pa., U.S.A. Typical compositions will be either oral or solutions for intravenous infusion. Typical dosage forms will be tablets (including coated tablets and "caplets") or capsules (including hard gelatin capsules and "softgels") for oral administration, solutions for intravenous infusion, and solids (especially lyophilized powders) for reconstitution as solutions for intravenous infusion.

Depending on the intended mode of administration, the pharmaceutical compositions may be in the form of solid, semi-solid or liquid dosage forms, preferably in unit dosage form suitable for single administration of a precise dosage. In addition to an effective amount of the active compound(s), the compositions may contain suitable pharmaceutically-acceptable excipients, including adjuvants which facilitate processing of the active compound(s) into preparations which can be used pharmaceutically. "Pharmaceutically acceptable excipient" refers to an excipient or mixture of excipients which does not interfere with the effectiveness of the biological activity of the active compound(s) and which is not toxic to the host to which it is administered.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet or capsule, or it may be an aqueous or nonaqueous solution, suspension or syrup. Tablets and capsules are preferred oral administration forms. Tablets and capsules for oral use will generally include one or more commonly used excipients such as lactose and corn starch. Lubricating agents, such as magnesium stearate, are also typically added. When liquid suspensions are used, the active compound may be combined with emulsifying and suspending excipients. If desired, flavoring, coloring and/or sweetening agents may be added as well. Other optional excipients for incorporation into an oral composition include preservatives, suspending agents, thickening agents, and the like.

Injectable pharmaceutical compositions can be prepared in conventional forms, either as liquid solutions or suspensions, solid forms suitable for solubilization or suspension in liquid prior to injection, or as emulsions or liposomal compositions. The sterile injectable composition may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media.

The pharmaceutical compositions of this invention may also be formulated as lyophilized powders for parenteral administration. Powders may be reconstituted by addition of water or other primarily aqueous medium and then further diluted with a suitable diluent prior to use. The liquid diluent is generally a buffered, isotonic, aqueous solution. Examples of suitable diluents are isotonic saline solution, aqueous 5% dextrose solution, and buffered sodium or ammonium acetate solution. Pharmaceutically acceptable solid or liquid excipients may be added to enhance or stabilize the composition, or to facilitate preparation of the composition.

Typically, a pharmaceutical composition of the present invention is packaged in a container with a label, or instructions, or both, indicating use of the pharmaceutical composition in the treatment of cancer and/or an autoimmune disease.

The pharmaceutical composition may additionally contain one or more other pharmacologically active agents in addition to a compound of this invention. These additional active agents will typically be useful in treating cancer, or for enhancing the treatment of cancer by compounds of this invention.

Methods of Using the Compounds

The compounds of the first aspect of this invention have activity against human cancer cell lines, as demonstrated in the In vitro and In vivo Examples below, and are therefore considered to be useful as chemotherapeutic agents for the treatment of human cancers. Further, because the compounds of the first aspect of this invention release "cyclophosphamide mustard" by the mechanism below:

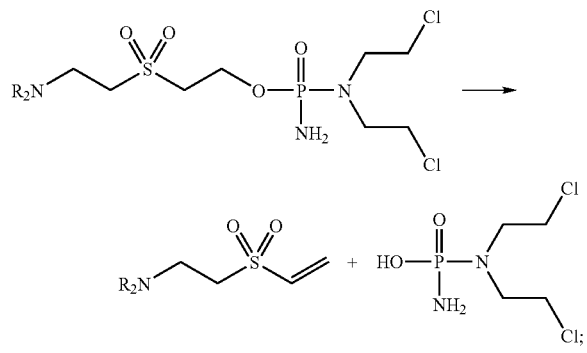

they are expected to be useful as agents for the treatment of any disease in which cyclophosphamide is a useful treatment, such as those cancers and autoimmune diseases mentioned in paragraph [0008].

Thus, the third aspect of this invention includes methods of treating cancer and autoimmune diseases in humans by administering a therapeutically effective amount of a compound of the first aspect of this invention, or a pharmaceutical composition of the second aspect of this invention, to the human; and the use of the compounds of the first aspect of this invention in the manufacture of medicaments for the treatment of cancer and autoimmune diseases in humans. Optionally, the methods further comprise treating the human with another therapy, such as a therapy already conventional for the disease being treated.

The amount of the compound of the first aspect of this invention that is administered to the human (either alone or, more usually, in a composition of the second aspect of this invention) should be a therapeutically effective amount when used alone or when used in conjunction with the another therapy (if the compound of the first aspect of this invention is administered in conjunction with another therapy); and similarly the amount of the another therapy that is administered to the human (if the compound of the first aspect of this invention is administered in conjunction with another therapy) should be a therapeutically effective amount when used in conjunction with the compound of the first aspect of this invention. However, the therapeutically effective amount of either the compound of the first aspect of this invention and the amount of the another therapy when administered in combination chemotherapy may each be less than the amount which would be therapeutically effective if delivered to the human alone. It is common in cancer therapy, though, to use the maximum tolerated dose of the or each therapy, with a reduction only because of common toxicity of the therapies used or potentiation of the toxicity of one therapy by another. Because of the lack of cross-resistance of canfosfamide, for example, with several common chemotherapeutic agents, and its relative lack of clinically severe toxicity, especially its lack of clinically severe hematological toxicity, it is expected that compounds of the first aspect of this invention will be administrable at essentially their maximum tolerated dose as a single agent, and no reduction in the amount of the another anticancer therapy will be required.

The compounds of the first aspect of this invention, or pharmaceutical compositions of the second aspect of this invention, are thus used to treat cancer and autoimmune diseases in humans requiring such treatment, by administering a therapeutically effective amount of the chosen compound or composition. For cancers, therapeutically effective amounts of compounds of the invention are in the range of 10-10,000 mg/m$^2$, for example, 30-3000 mg/m$^2$ or 100-1000 mg/m$^2$. Dosing may be at 1-35 day intervals; for example, about 500-1000 mg/m$^2$ at 1-5 week intervals, especially at 1, 2, 3, or 4 week intervals, or at higher frequencies including as frequently as once/day for several (e.g. 5 or 7) days, with the dosing repeated every 2, 3, or 4 weeks, or constant infusion for a period of 6-72 hours, also with the dosing repeated every 2, 3, or 4 weeks. For autoimmune diseases, the dosages will be significantly lower, and suitable dosages and dose frequencies will be readily determinable by a person of ordinary skill in the art having regard to that skill, the knowledge of suitable dosing for canfosfamide and for cyclophosphamide, and this disclosure. No unacceptable toxicological effects are expected when compounds of the invention are administered in accordance with the present invention.

For cancer, suitable dosing for the other therapy (if the compound of the first aspect of this invention is used in combination) will be the dosing already established for that therapy, as described in such documents as those listed in paragraph [0024]. Such dosing varies widely with the therapy: for example, capecitabine (2500 mg/m² orally) is dosed twice daily for 2 weeks on and 1 week off, imatinib mesylate (400 or 600 mg/day orally) is dosed daily, rituximab is dosed weekly, paclitaxel (135-175 mg/m²) and docetaxel (60-100 mg/m²) are dosed weekly to every three weeks, carboplatin (4-6 mg/mL·min) is dosed once every 3 or 4 weeks (though the doses may be split and administered over several days), nitrosourea alkylating agents such as carmustine are dosed as infrequently as once every 6 weeks. Radiotherapy may be administered as frequently as weekly (or even within that split into smaller dosages administered daily).

A person of ordinary skill in the art of therapy for cancer or autoimmune diseases will be able to ascertain a therapeutically effective amount of the compound of the first aspect of this invention and a therapeutically effective amount of another therapy for a given disease and stage of disease without undue experimentation and in reliance upon personal knowledge and the disclosure of this application.

Combination therapies for cancer may include, for example, the combination administration of a compound of the first aspect of this invention with a platinum compound such as carboplatin or cisplatin, optionally in further combination with gemcitabine or a taxane such as docetaxel or paclitaxel; with gemcitabine; with a taxane; with an anthracycline such as doxorubicin or liposomal doxorubicin; with oxaliplatin, optionally in further combination with capecitabine or fluorouracil/leucovorin; and with gemcitabine or a platinum compound such as carboplatin or cisplatin, in further combination with a vinca alkaloid such as vinorelbine.

EXAMPLES

The following examples illustrate the preparation of compounds of this invention, and their activity in predictive in vitro and in vivo anticancer assays.

Preparative and Synthetic Examples

The compounds of this invention are prepared by conventional methods of organic chemistry. See, for example, Larock, "Comprehensive Organic Transformations", (1989), Wiley-VCH, New York, N.Y., U.S.A. The compounds of this invention can be synthesized, generally following the synthetic scheme illustrated earlier in this application, as shown in the following examples or by modifying the exemplified synthesis by means known to those of ordinary skill in the art.

Preparative Example 1

Preparation of 2-[2-(diethylamino)ethylthio]ethanol from 2-(diethylamino) ethanethiol.

2-(Diethylamino)ethanethiol hydrochloride (5.0 g, 29 mmol) was added to a 250 mL round-bottom flask, 20 mL methanol was added, and the solution cooled in an ice bath with stirring. Sodium hydroxide (2.34 g, 58 mmol), dissolved in water (15 mL), was added, followed by slow addition of 2-bromoethanol (5.9 g, 47 mmol). Stirring was continued while the reaction mixture was allowed to warm to room temperature overnight. The methanol and water were removed under reduced pressure, and the residue dissolved in ethyl acetate (100 mL), washed with water (3×20 mL), dried over magnesium sulfate, and concentrated under reduced pressure to give 2-[2-(diethylamino)-ethylthio]ethanol as a yellow oil (4.5 g, 87% yield). LC-MS (ES⁺): m/z=178 [$C_8H_{19}NOS+H^+$] for product peak. A 1.0 g aliquot of the crude 2-[2-(diethylamino)ethylthio]ethanol was purified by flash chromatography on silica cartridges, eluting with a gradient of 100% hexane to 100% ethyl acetate over 5 minutes, to give 0.78 g pure 2-[2-(diethylamino)ethylthio]ethanol as a colorless oil after evaporation of the solvents, and the remaining 3.5 g similarly purified, eluting with a gradient of 100% hexane to 100% ethyl acetate over 20 minutes, to give an additional 3.11 g pure 2-[2-(diethylamino)ethylthio]ethanol.

Preparative Example 2

Preparation of 2-[2-(diethylamino)ethylthio]ethanol from 2-(diethylamino) ethyl bromide To a solution of 2-mercaptoethanol (1.5 mL, 1.7 g, 22 mmol) in methanol (30 mL) was added with stirring sodium carbonate (4 g, 38 mmol), followed by 2-(diethylamino)ethyl bromide hydrobromide (5.0 g, 19 mmol). The reaction mixture was stirred overnight at room temperature and then filtered. The filtrate was concentrated under reduced pressure to give 2-[2-(diethylamino)ethylthio]-ethanol as a clear oil.

Preparative Example 3

Preparation of N,N-bis(2-chloroethyl)phosphoramidic dichloride

Bis(2-chloroethyl)amine hydrochloride (6.3 g, 35 mmol), suspended in 80 mL dichloromethane, was cooled to −78° C. under argon and stirred. A solution of phosphoryl chloride (5.41 g, 35 mmol) in 10 mL dichloromethane, followed by a solution of triethylamine (3.53 g, 70 mmol) in 10 mL dichloromethane, was added slowly by syringe. Stirring was continued while the reaction mixture was allowed to warm to room temperature overnight. The reaction mixture was washed with 0.01N hydrochloric acid (3×25 mL), dried over magnesium sulfate, and concentrated under reduced pressure to give N,N-bis(2-chloroethyl)phosphoramidic dichloride as a light orange oil that solidified on standing (7.9 g, 87% yield). A 2.2 g aliquot of the crude N,N-bis(2-chloroethyl)phosphoramidic dichloride was purified by flash chromatography on a 12 g silica cartridge, eluting with a gradient of 100% hexane to 67% hexane/33% ethyl acetate over 10 minutes followed by 67% hexane/33% ethyl acetate for a further 10 minutes, to give 1.5 g pure N,N-bis(2-chloroethyl)phosphoramidic dichloride as a white solid after evaporation of the solvents. MS (ES): m/z=275 [$C_4H_8Cl_4NOP+NH_4^+$].

Synthetic Example

Preparation of 2-{[2-(diethylamino)ethyl]sulfonyl}ethyl N,N-bis(2-chloroethyl)phosphorodiamidate, compound 1A, as its hydrochloride salt 2-{[2-(Diethylamino)ethyl]thio}ethyl N,N-bis(2-chloroethyl)phosphorodiamidate. To a solution of 2-[2-(diethylamino)ethylthio]ethanol (420 mg, 2.4 mmol) in tetrahydrofuran, cooled to −78° C., was added with stirring lithium bis(trimethylsilyl)amide (1.0M in tert-butyl methyl ether, 2.62 mL, 2.62 mmol), followed by a solution of N,N-bis(2-chloroethyl)phosphoramidic dichloride (680 mg, 2.62 mmol) in tetrahydrofuran (10 mL). The orange reaction mixture was stirred at −78° C. for 90 minutes, then allowed to warm to −20° C. and ammonia gas bubbled through it for 10 minutes. The reaction mixture was stirred for an additional 10 minutes, then poured into a separatory funnel containing water (200 mL) and dichloromethane (200 mL). The organic and aqueous layers were separated, and the aqueous layer washed with dichloromethane (3×200 mL). The organic layer and washings were combined, dried over magnesium sulfate, filtered, and the filtrate concentrated under reduced pressure to give a yellow oil. The oil was purified by chromatography on a 25 g silica column, eluting with 90% chloroform/10% (5% ammonium hydroxide in methanol), to give 2-{[2-(diethylamino)ethyl]thio}ethyl N,N-bis(2-chloroethyl)phosphorodiamidate as a clear oil, 97% pure by HPLC. MS (ES): m/z=380 $[C_{12}H_{28}Cl_2N_3O_2PS+H^+]$.

2-{[2-(diethylamino)ethyl]sulfonyl}ethyl N,N-bis(2-chloroethyl)phosphorodiamidate hydrochloride. To a solution of 2-{[2-(diethylamino)ethyl]thio}ethyl N,N-bis(2-chloroethyl)-phosphorodiamidate (500 mg, 1.3 mmol) in N,N-dimethylformamide (5 mL) at 0° C. was added trifluoroacetic acid (506 µL, 780 mg, 6.8 mmol), and the mixture was stirred at 0° C. for 10 minutes; then peroxyacetic acid (32% in dilute acetic acid, 608 µL, 2.9 mmol) was added over 10 minutes. The reaction mixture was allowed to warm to room temperature and was then diluted with ethyl acetate (approximately 100 mL) and washed twice with a 1:1 mixture of saturated aqueous sodium bicarbonate and 0.2M sodium hydrosulfite (approximately 100 mL). The organic layer was dried over magnesium sulfate, filtered, and acidified with an approximate 2-fold excess of hydrogen chloride (4M in dioxane). The solution was concentrated under reduced pressure to give 420 mg (77% yield) of 2-{[2-(diethylamino)ethyl]sulfonyl}ethyl N,N-bis(2-chloroethyl)phosphorodiamidate hydrochloride as a clear oil. MS (ES): m/z=412 $[C_{12}H_{28}Cl_2N_3O_4PS+H^+]$. $^1$H NMR (CDCl$_3$): δ 4.75 (b, 2H), 4.55-4.53 (m, 1H), 4.36-4.34 (m, 1H), 3.92-3.76 (m, 4H), 3.67 (t, 4H), 3.60-3.42 (m, 6H), 3.30-3.26 (m, 4H), 1.41 (t, 6H). $^{31}$P NMR (CDCl$_3$): δ 18.98 (s, 1P).

Other compounds of formula A may be similarly prepared. Other salts of compounds of formula A may similarly be prepared by using the appropriate acids, preferably in solvents that permit the isolation of the acid addition salts as solids.

In vitro Example

Cytotoxicity/Growth Inhibition Assay

The following examples illustrate the beneficial effect of the compounds of this invention against human cancer cell lines in vitro. These results are considered predictive of efficacy in human cancer chemotherapy, as other anticancer agents tested in these assays have shown anticancer activity in humans.

The human cancer cell line DLD-1 (colorectal adenocarcinoma) was obtained from the American Type Culture Collection, Manassas, Va., U.S.A. The CellTiter-Glo assay kit was obtained from Promega Corporation, Madison, Wis., U.S.A. All products were used in accordance with manufacturer's directions. All assays were conducted in triplicate wells, with dimethyl sulfoxide (DMSO) solvent control. The extent of cell growth was expressed as a percentage of the signal from the solvent control wells.

Log-phase cells were trypsinized, collected by centrifugation, and resuspended in a small volume of fresh medium, and the density of viable cells was determined following Trypan Blue staining. Cells were diluted in fresh media ($3 \times 10^3$ cells/mL for DLD-1), and added at 150 µL/well to 96-well plates, and incubated for several hours to allow attachment in the case of adherent cells. Compound 1A and canfosfamide, as their hydrochloride salts, dissolved in DMSO, were diluted 50-fold with fresh medium and the diluted solutions immediately added at 50 µL/well to the cell suspensions, giving final compound concentrations between 0.1 µM and 200 µM and a final DMSO concentration of 0.5%. The cells were cultured for approximately three doubling times (4 days). The cells were then collected by centrifugation, and 100 µL of the culture supernatant was replaced by the CellTiter-Glo reagent. After incubation for 10 minutes at room temperature, and the plate was read with a luminometer. The compounds showed the following activity (IC$_{50}$) in this assay: compound 1A, 13 µM; canfosfamide, 11 µM.

In vivo Example

MiaPaCa-2 Xenograft Assay, Intraperitoneal Administration

Male athymic nu/nu mice, 6-8 weeks old (approximately 20 g), were implanted subcutaneously in the right fore flank with 20-30 mg pieces of MIA PaCa-2 tumor harvested from similar nu/nu mice that had previously been implanted with the MIA PaCa-2 tumor. Ten days after tumor transplantation, when the tumor weight was approximately 150-550 mg, the mice were assigned to treatment groups such that each treatment group had a similar average tumor weight at the start of treatment. A group of mice was treated with compound 1A as the hydrochloride salt dissolved in aqueous 5% dextrose, at 100 mg/Kg by intraperitoneal injection once/day for 5 consecutive days; with vehicle and cyclophosphamide (30 mg/Kg) also administered by intraperitoneal injection for the same time. Tumor mass was estimated from volume on days 10, 13, and 17; and measured at autopsy on day 19 after transplantation. Compound 1A hydrochloride at 100 mg/Kg, with 83% tumor mass inhibition relative to vehicle, was as potent as cyclophosphamide at 30 mg/Kg, with 84% inhibition.

Compound 1A was safe and non-toxic at the dose tested.

Formulation and Therapeutic Examples

Formulation Example 1

Pharmaceutical Composition for Oral Administration

A solid pharmaceutical composition for oral administration is prepared by combining the following:

| Compound of this invention | 25.0% w/w |
|---|---|
| Magnesium stearate | 0.5% w/w |
| Starch | 2.0% w/w |
| Hydroxypropylmethylcellulose | 1.0% w/w |
| Microcrystalline cellulose | 71.5% w/w | and the mixture is compressed to form tablets or filled into hard gelatin capsules containing, for example, 100 mg of the compound of this invention. Tablets may be coated, if desired, by applying a suspension of a film-forming agent (for example, hydroxypropylmethylcellulose), pigment (for example, titanium dioxide), and plasticizer (for example, diethyl phthalate), and drying the film by evaporation of the solvent.

Formulation Example 2

Pharmaceutical Composition for IV Administration

A pharmaceutical composition for IV administration is prepared by dissolving a compound of this invention, for example as a pharmaceutically acceptable salt, to a concentration of 1% w/v in phosphate-buffered saline; and the solution is sterilized, for example by sterile filtration, and sealed in sterile containers containing, for example, 100 mg of a compound of this invention.

Alternatively, a lyophilized composition is prepared by dissolving a compound of this invention, again for example as a pharmaceutically acceptable salt, in a suitable buffer, for example the phosphate buffer of the phosphate-buffered saline mentioned above, sterilizing the solution and dispensing it into suitable sterile vials, lyophilizing the solution to remove the water, and sealing the vials. The lyophilized composition is reconstituted by the addition of sterile water, and the reconstituted solution may be further diluted for administration with a solution such as 0.9% sodium chloride intravenous infusion or 5% dextrose intravenous infusion.

Therapeutic Example

Therapy with Compounds of this Invention

A compound of this invention, diluted in 5% dextrose intravenous infusion, is administered intravenously over 30 minutes to a patient suffering from metastatic ovarian carcinoma at an initial dose of 100 mg/m$^2$; and this dose is increased to 250 mg/m$^2$, 500 mg/m$^2$, 750 mg/m$^2$, and 1000 mg/m$^2$. The compound is administered at 1-week intervals. The same dose escalation is administered at 2- and 3-week intervals to other patients suffering from the same cancer.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

We claim:
1. A compound of formula A:

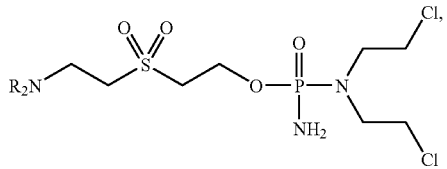

or its salt,
where each R is independently methyl, ethyl, propyl, or isopropyl, or —NR$_2$ together is pyrrolidin-1-yl or piperidin-1-yl.

2. The compound of claim 1 in solid form.
3. The compound of claim 1 where each R is independently methyl, ethyl, or isopropyl.
4. The compound of claim 3 where each R is the same.
5. The compound of claim 4 where each R is ethyl.
6. The compound of claim 1 that is a salt of the compound of formula A.
7. The compound of claim 6 in solid form.
8. A pharmaceutical composition comprising a compound of claim 1 and an excipient.
9. A method of preparing a compound of formula A:

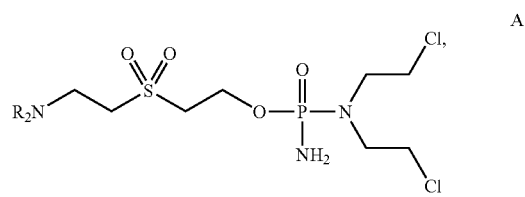

or its salt,
where each R is independently methyl, ethyl, propyl, or isopropyl, or —NR$_2$ together is pyrrolidin-1-yl or piperidin-1-yl; comprising:
(a) oxidizing a corresponding compound of formula B:

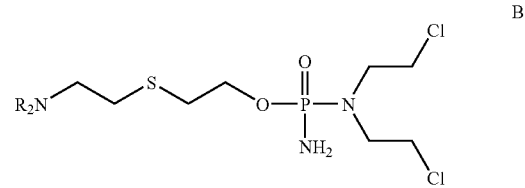

to the compound of formula A,
optionally followed by one or more of:
(b) forming a salt of a compound of formula A;
(c) converting a salt of a compound of formula A to another salt of a compound of formula A; and
(d) converting a salt of a compound of formula A to the non-salt form of the compound of formula A.
10. A compound of formula B:

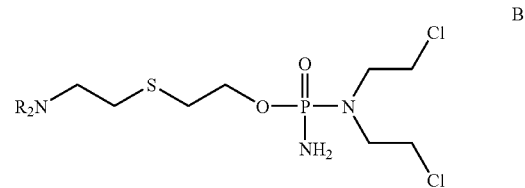

or its salt,
where each R is independently methyl, ethyl, propyl, or isopropyl, or —NR$_2$ together is pyrrolidin-1-yl or piperidin-1-yl.
11. The compound of claim 10 where each R is independently methyl, ethyl, or isopropyl.
12. The compound of claim 11 where each R is the same.
13. The compound of claim 12 where each R is ethyl.

* * * * *